United States Patent [19]

Ulert

[11] Patent Number: 4,867,268
[45] Date of Patent: Sep. 19, 1989

[54] SANITARY STETHOSCOPE

[76] Inventor: Izaak A. Ulert, 3651 Dumbarton, Houston, Tex. 77025

[21] Appl. No.: 142,131

[22] Filed: Jan. 7, 1988

[51] Int. Cl.⁴ .......................................... H04R 25/00
[52] U.S. Cl. .................................. 181/137; 181/126; 181/131; 181/171; 381/188
[58] Field of Search ............... 181/131, 137, 126, 171; 381/188, 67

[56] References Cited

U.S. PATENT DOCUMENTS

| | | | |
|---|---|---|---|
| 2,651,380 | 9/1953 | Braidenburg | 181/137 |
| 2,893,507 | 7/1959 | Friedman | 181/137 |
| 3,587,776 | 6/1971 | Haiken | 181/137 |
| 3,766,361 | 10/1973 | Swinyar et al. | 181/131 X |
| 3,867,925 | 2/1975 | Ersek | 181/131 X |
| 4,007,806 | 2/1977 | Nobles, Jr. | 181/131 |
| 4,458,778 | 7/1984 | Bloom | 181/137 X |
| 4,461,368 | 7/1984 | Plourde | 181/131 |

Primary Examiner—B. R. Fuller

[57] ABSTRACT

A sanitary stethoscope which prevents carrying potentially infectious matter from one patient to the next comprises a modified stethoscope head or diaphragm-retaining ring and a quick-insert/quick-release replaceable diaphragm. The diaphragm is suitably held in place on the stethoscope by means of a projection on the diaphragm surface which fits into a groove on the stethoscope head or diaphragm-retaining ring, preferably with provision for magnetic attraction. Means for facilitating easy exchange of diaphragms comprise specially designed diaphragm dispensers and diaphragm storage containers or cartridges. The diaphragm dispensers may be heated to maintain the diaphragms at a temperature comfortable to the touch.

18 Claims, 3 Drawing Sheets

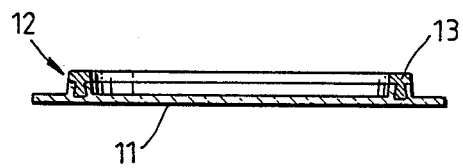
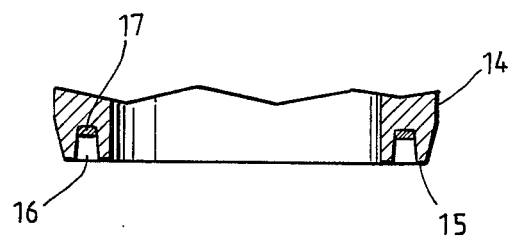
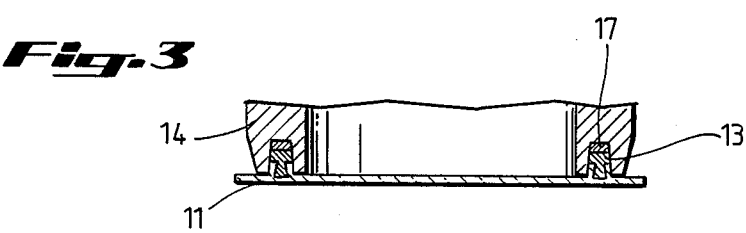
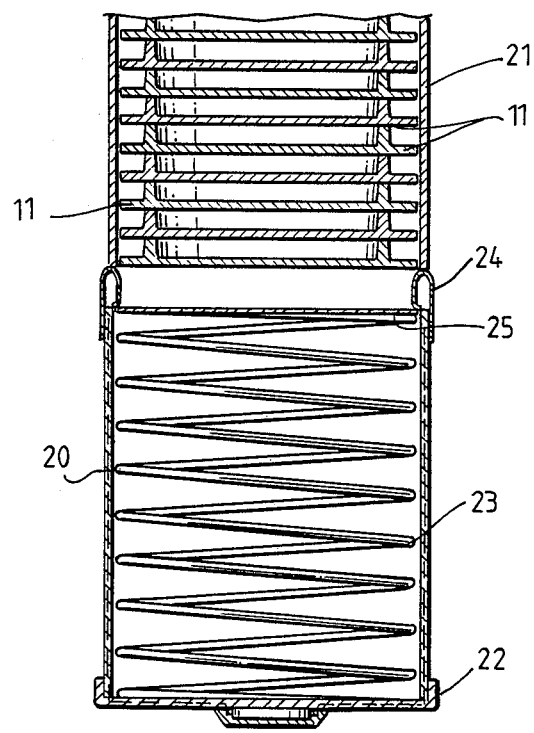
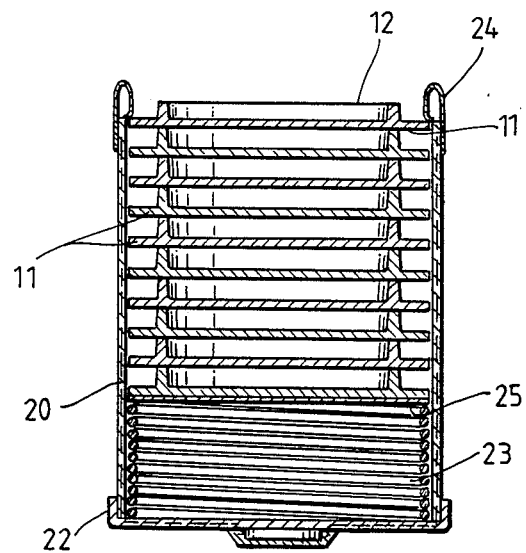

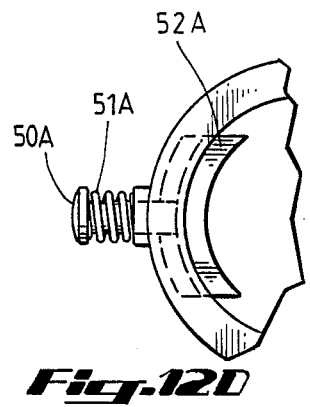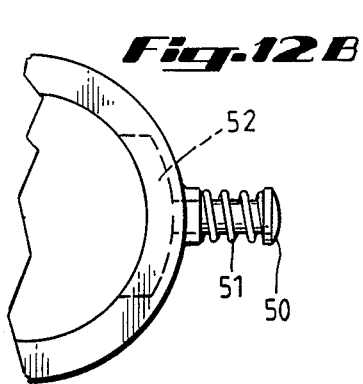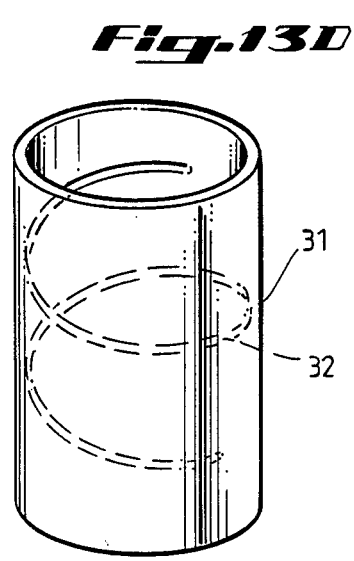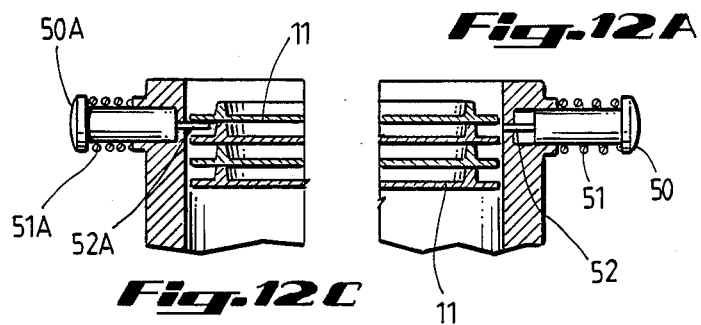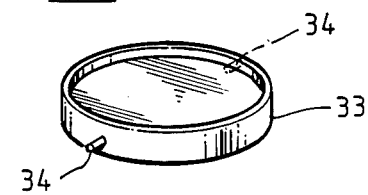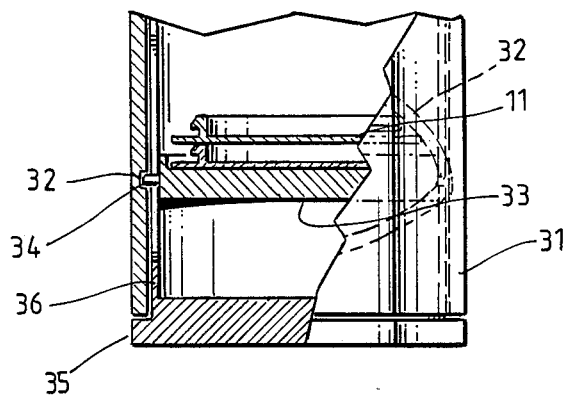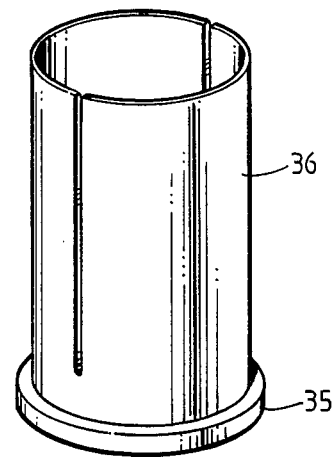

SANITARY STETHOSCOPE

DESCRIPTION

1. Field of the Invention

This invention relates to medical stethoscopes. More particularly, it relates to stethoscopes which have quick-insert/quick-release, replaceable diaphragms, to dispensers for such diaphragms and to containers for replacement diaphragms.

2. Background Art

The use of medical stethoscopes is well known. In the conventional use of the stethoscope by physicians, the stethoscope is not sterilized between examinations of patients. Typically, as the stethoscope is directly applied to the skin, the diaphragm will become contaminated and has the potential of contaminating the next patient.

The potential of the stethoscope to act as a source of infection has been recognized. See, for example, "Contaminated Stethoscopes: A Potential Source of Nosocomial Injections" by Mangi et al, Yale Journal of Biology and Medicine, 45,600–45,604 (1972).

A removable diaphragm cover for stethoscopes is the subject of U.S. Pat. No. 4,461,368 to Plourde. It comprises a flexible membrane sheet mounted on a rigid rim which clips over the outer edge of the stethoscope head and thus covers the diaphragm. The Plourde patent also describes other, less relevant prior art.

BRIEF SUMMARY OF THE INVENTION

The Plourde patent describes the reasons for and the advantages of providing an uncontaminated diaphragm surface for each examination. While the removable diaphragm cover of Plourde provides the desired hygienic condition of the stethoscope, it lacks ease of quick interchange. It also interposes a second layer of material between the source of sound and the ear, which has the potential of diminishing or distorting the sound.

Although it is over five years since the Plourde device was invented and more than three years since it was patented, it apparently has not found its use in medical practice. The present invention is intended to make use of uncontaminated diaphragms as quick and easy as possible, to encourage their use by the busy physician or nurse.

According to this invention, there is provided a stethoscope designed to be used with a dispenser of replacement diaphragms. The stethoscope head and diaphragm are designed to permit the used diaphragm to be easily pulled off and a fresh diaphragm to be easily attached by inserting the head of the stethoscope into the dispenser of replacement diaphragms.

The present invention provides all the advantages described at length in the Plourde patent in addition to providing for quick release and quick replacement, which encourages use.

BRIEF DESCRIPTION OF THE DRAWING

This invention is further described by reference to the drawing, wherein like numbers refer to like parts, and wherein:

FIG. 1 is a sectional view of a diaphragm according to the invention;

FIG. 2 is a sectional view of the head of a stethoscope according to the invention;

FIG. 3 is a sectional view of the diaphragm attached to the stethoscope head;

FIG. 4 is a sectional view of a diaphragm dispenser with a cartridge of diaphragm in position for insertion thereinto;

FIG. 5 is a sectional view of a diaphragm dispenser with a set of diaphragms inserted;

FIGS. 12A and 12C are sectinal views and FIGS. 12B and 12D are plan views of another alternative design of the top of a diaphragm dispenser; and FIG. 13A is a view in partial section of a different alternative design of a diaphragm dispenser; FIGS. 13B–13D are isometric views of parts of the same dispenser.

DETAILED DESCRIPTION OF THE INVENTION

Figure 5A:
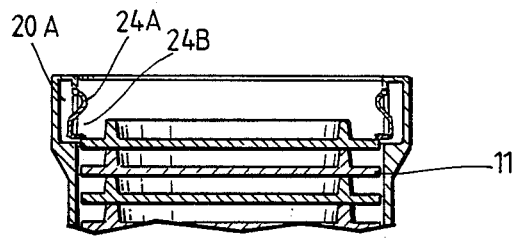
FIG. 5A is a detail of an alternative design of a part of a diaphragm dispenser.

This invention consists of a combination of a stethoscope, exchangeable diaphragms for the stethoscope head, diaphragm dispensers, cartridges for spare diaphragms, and of various cooperating parts, including a modified diaphragm-retaining ring for conventional stethoscopes.

More specifically, the invention consists of a specially designed stethoscope head or diaphragm-retaining ring of a stethoscope, a specially designed disposable diaphragm, and devices for storing and dispensing such diaphragms. In a preferred embodiment, the diaphragms have on one surface a ringlike projection; the stethoscope head has, on its outer face, a ringlike groove designed to accept the projection on the diaphragm. The diaphragm is held tightly in place by the fit of the projection in the groove or by the combination of said fit and magnetic attraction. When assembled, the diaphragm projects in whole or in part, as by a tab, beyond the rim of the stethoscope head, to permit it to be quickly and easily pulled off. In order to facilitate quick exchange of diaphragms, there is provided a diaphragm dispenser which stores a set of diaphragms and is designed to permit insertion of the stethoscope head to mate with the topmost diaphragm.

The diaphragm is constructed of a rigid material of the type conventionally employed in commercial stethoscopes.

In the preferred embodiment, the circular projection consists of or contains metal which is either magnetized or magnetizable. Most suitably, the projection on the diaphragm is magnetic and the stethoscope head or diaphragm retaining ring is made of magnetized or magnetizable material or contains sufficient magnetizable material in the groove which receives the projection to provide the required firm hold.

In an alternative mode, the groove and projection are of a tight-fitting design which permits attaining firm adhesion of the diaphragm by application of moderate pressure and also permits ready release. Several embodiments of such designs are illustrated below. Also useful may be the designs used in Ziploc ® freezer bags of Dow Chemical Company, wherein at least the projection is of flexible plastic.

A conventional stethoscope may be converted for use according to the invention by replacing the conventional diaphragm-retaining ring with a ring fitted with a groove according to the invention.

Turning now to the drawings, FIGS. 1-3 illustrate a preferred mode of the invention, in which the diaphragm is held to the stethoscope head by magnetic attraction.

FIG. 1 is a vertical section through a circular diaphragm 11, made of a suitable rigid non-magnetic material, which has on its inner surface (with respect to the stethoscope) a ridge or projection 12 which contains a magnetic insert 13.

FIG. 2 is a vertical section through a stethoscope head 14 which is adapted to accept the diaphragm of FIG. 1. The structure of medical stethoscopes is well known and is therefore not shown in the drawing. The invention is applicable to any typical diaphragm-type medical stethoscope. Such stethoscopes have a threaded diaphragm-retaining ring which is screwed onto the stethoscope head to hold a diaphragm in place between itself and the stethoscope head. In FIG. 2, 14 represents the outer portion of the head of a stethoscope. If it is a converted conventional stethoscope, 14 would be a ring, threaded to fit onto the stethoscope head. If the stethoscope itself is designed according to this invention, 14 represents the outer portion of the head itself. Stethoscopes are typically made of non-magnetizable material, such as aluminum. Head 14, as shown, is non-magnetizable. It may be metal or non-metallic synthetic. It has in its outer plane surface 15 a groove 16. At the bottom of the groove is a ring 17 of magnetizable material. Groove 16 is adapted to receive ridge 12 with very little clearance. As shown, groove 16 and ridge 12 are slightly tapered to facilitate insertion.

FIG. 3 shows diaphragm 11 inserted into stethoscope head 14. As shown, the outermost part of head 14 has a slight inward taper, so that its circumference at the outer plane surface is less than the circumference away from the surface. This permits the edge of diaphragm 11 or tabs on the diaphragm to protrude slightly, which is desirable for quick, easy removal of a diaphragm without having the diameter of the diaphragm exceed that of the body of the stethoscope head. However, certain precautions are required, as discussed below in connection with FIG. 5A.

The shape in which the metal is present in ridge or projection 12 and groove 16 is not critical, provided a sufficient degree of magnetic attraction is achieved. Thus, while metal insert 13 is shown as a ring with an essentially T-shaped cross section, it may also, for example, be a wire with circular cross section, positioned near the surface of the projection.

A busy physician, nurse or medical technician, seeing patient after patient, would resist using replaceable stethoscope diaphragms if any significant amount of manipulation were required for replacing a used diaphragm with a fresh one. Accordingly, an important feature of this invention in its broadest aspect is the provision of a device which simplifies such replacement. In essence, this comprises (1) a diaphragm dispenser which is adapted to hold a set of diaphragms and to admit the head of a stethoscope so that it contacts the topmost diaphragm, mates with it, and is withdrawn with the diaphragm firmly attached and (2) holders or cartridges which contain a number of diaphragms and which are adapted to permit easy insertion of the cartridge or of the set of diaphragms into the dispenser.

Figure 6:
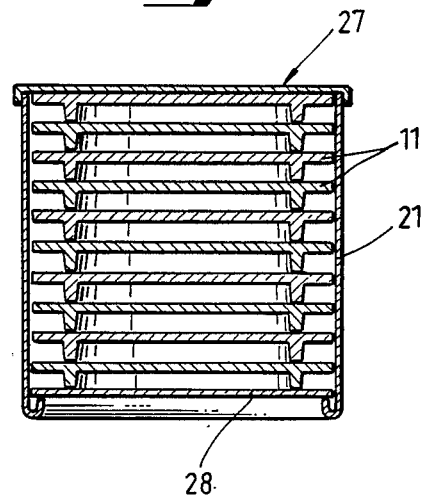
FIG. 6 is a sectional view of a spare diaphragm cartridge.

One embodiment of the invention is shown in FIGS. 4-6. FIG. 4 shows a cartridge 21 in position for the diaphragms to be inserted in dispenser 20; FIG. 5 shows the dispenser with the diaphragms inserted for use; and FIG. 6 shows a separate spare cartridge for use as in FIG. 4.

In FIGS. 4-6, shown in vertical section, 11 represents diaphragms such as those of FIG. 1. In dispenser 20, 23 is a spring, in position to urge the stack of diaphragms upward and 24 is a spring adapted to hold the topmost diaphragm in place against the urging of spring 23, but capable of being sufficiently displaced outwardly to permit insertion of the head of a stethoscope or of a new set of diaphragms from a cartridge. Spring 24 may cover the whole rim of the dispenser, but it is sufficient if separate springs 24, extending only a few degrees of arc, are present in three or four locations suitably spaced around the rim. Dispenser 20 further contains a top plate or divider 25 which is adapted to slide in the dispenser; it is located on top of spring 23 and acts as a stop against spring 24 when the dispenser is empty. Spring 23 may be referred to as a pushing spring and 24 as a holding spring. Dispenser 20, as shown, has a separate bottom plate 22 which may be removable to provide access to the pushing spring; it may be held in place by a pressure fit, or by threading, not shown. The bottom plate may be an integral part of dispenser 20, if desired. A dispenser with removable bottom plate may also be designed for insertion of spare diaphragms from the bottom of the dispenser. In that case, the bottom plate, pusher spring and divider plate are removed when replacement diaphragms are to be inserted.

In FIG. 6, a spare cartridge contains a removable cap 27 which holds the diaphragms in place until required, and a pusher plate 28 which is adapted to slide within the cartridge body. For use in a dispenser such as that of FIG. 4, cap 27 is removed from a spare cartridge 21, the cartridge is placed over the dispenser and the diaphragms are inserted into the dispenser by pushing down on plate 28. The empty cartridge may be discarded or reused.

It will be evident that, for insertion from the bottom of the dispenser, the cartridge will have to be modified by having the diaphragms inserted with the projection up, instead of down as shown in FIG. 6. In an appropriately designed dispenser, the whole cartridge can be inserted after removal of cap 27 and become part of the dispensing system.

A filled dispenser 20 is shown in FIG. 5. For use with a magnetic system such as shown in FIGS. 1-3, stethoscope head 14 is pushed against the topmost diaphragm. Holding spring 24 moves out of the way to admit the stethoscope head. To permit use with stethoscopes which have a side connection tube, there is a slot, not shown, cut into the side of dispenser to accommodate the side connection tube when the stethoscope head enters the dispenser. When the stethoscope head contacts the diaphragm, ridge 12 fits into groove 16 and the magnetic attraction is sufficient to hold the diaphragm in place on the head. The stethoscope head can then be withdrawn ready for use, with the diaphragm in place. Pusher spring 23 then forces the next diaphragm to the top. When the last diaphragm has been used, a new set is inserted from a fresh cartridge.

Many variations of the mechanical features of this invention will be readily apparent to the person skilled in the art and can be employed within the scope of the invention. A few modifications are illustrated in FIGS. 5A and 7–13.

FIG. 5A shows a detail of a modification of FIG. 5 which is designed to avert the problem, referred to above, which could be caused by the taper of stethoscope head 14 as shown in FIG. 3. If a tapered stethoscope head were to be used in the dispenser of FIG. 5, it is possible that upon the stethoscope head being withdrawn from the dispenser, spring 24 could catch on the protruding edge of the diaphragm and cause the diaphragm to be dislodged. Use of small tabs, rather than a full-circle protruding edge reduces the chances of this happening. However, the problem is completely avoided by the design of FIG. 5A. In FIG. 5A, spring 24A, like spring 24 of FIG. 5, is designed to move out of the way when the stethoscope head is inserted into the dispenser. In this embodiment, the spring is fixed at its top to the inner part of a hollow extension 20A of the dispenser wall. When a stethoscope with a tapered head has been inserted, the full width of the stethoscope head flattens spring 24A while the tapered end contacts the topmost diaphragm. As the top bulge of the spring is flattened, it forces the flat bottom part 24B to withdraw into the hollow space and keeps it out of the way of the diaphragm when the head is withdrawn from the dispenser. Precautions are also required to prevent the bulge of spring 24A from interfering with the diaphragm as the stethoscope head is withdrawn. This can be accomplished by several different means. For example, the diaphragm may be designed so that its projecting rim or tabs have a diameter which is greater than that of the tapered end of the stethoscope head, but less than the distance measured between the innermost points of the bulge measured across the dispenser. In another method, tabs are employed whose diameter may be the same as the wide part of the stethoscope head, and spring 24A is not continuous around the rim of the dispenser but consists of two or more shorter segments, spaced to provide the required support but with sufficient intervals to accommodate the tabs; in that embodiment, means are provided to assure orientation of the diaphragms in the dispenser such that the tabs rise up through the open intervals.

Figure 7:
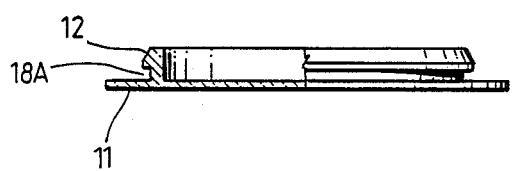
FIG. 7 is a view in partial section of an alternative design of a diaphragm according to the invention.
Figure 8:
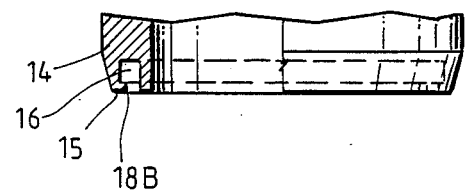
FIG. 8 is a view in partial section of the corresponding design of a stethoscope head.
Figure 9:
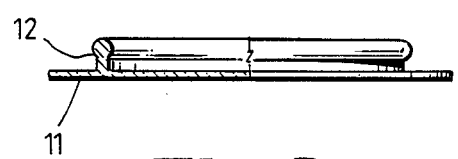
FIG. 9 is a view in partial section of another alternative design of a diaphragm according to the invention.
Figure 10:
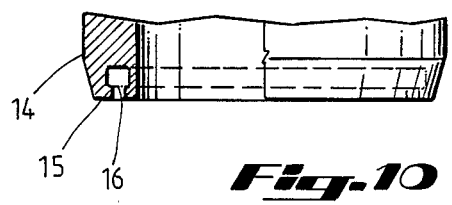
FIG. 10 is a view in partial section of the corresponding design of a stethoscope head.

FIGS. 7 and 9 illustrate two types of diaphragm which do not rely on magnetic attraction for firm attachment to a stethoscope head. They show two modifications of the structure of ridge 12. FIGS. 8 and 10 show the corresponding grooves 16 in the stethoscope head.

In FIGS. 7 and 8, ridge 12 has an indentation 18A and groove 16 has a corresponding lip 18B which fits into indentation 18A. At least one of projection 12 and lip 18B is sufficiently flexible to permit entrance of projection 12 into groove 16. It will be understood that both the projection and the groove are fully circular in order to assure the desired firm adherence of the diaphragm to the stethoscope head.

In FIGS. 9 and 10, projection 12 consists of a relatively narrow neck attached to the diaphragm and a wider ring of approximately circular cross section connected to the neck. Groove 16, correspondingly, has a narrow entrance which corresponds to the narrow neck of projection 12. Again, one or the other, or both, must be sufficiently flexible to permit ready entrance of the projection into the groove.

In the modifications in which the diaphragm is held in place on the stethoscope by the fit between ridge and groove, it is important that the topmost diaphragm in the holder be held firmly in place when the stethoscope head is pressed against it. FIGS. 11, 12 and 13 illustrate three designs which accomplish this objective.

Figure 11A:
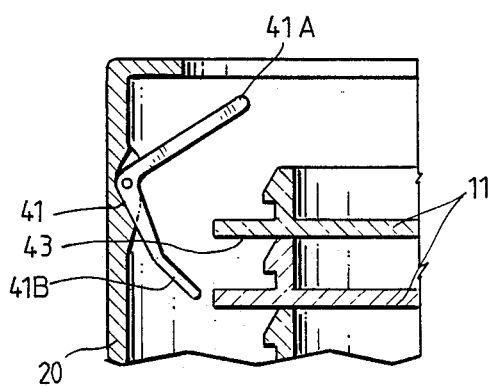
FIGS. 11A and 11B are sectional views of a detail of an alternative design of the top of a diaphragm dispenser.
Figure 11B:
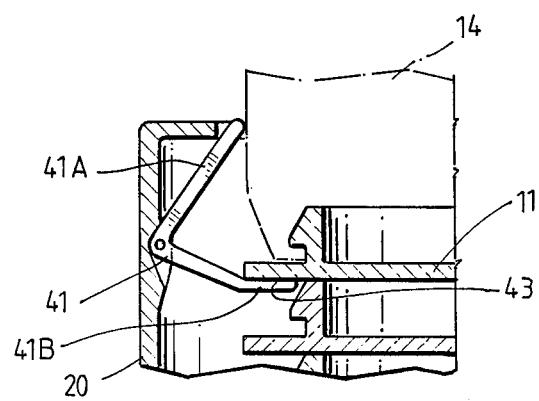

One mode of providing firm support for the topmost diaphragm, for use with a system which employs a pusher spring, is illustrated in FIGS. 11A and 11B. In lieu of holding spring 24, as illustrated in FIGS. 4 and 5, this system employs a hinged support arm 41, attached to the top of wall 20 of a diaphragm dispenser. FIG. 11A illustrates the position of support arm 41 after a top diaphragm has been removed, attached to a stethoscope head. FIG. 11B shows the position when a new diaphragm has been brought to the top and a stethoscope head 14 inserted for contact. As shown in FIG. 11A, support arm 41 has been pulled down by a spring, mounted, for example, at the pivot point, but not shown, into a positon in which it does not engage any diaphragm. As the column of diaphragms is raised, as by a pushing spring 23 as shown in FIGS. 4 and 5, the rim of diaphragm 43 pushes on the upper arm 41A, displacing it upward into a position in which stethoscope head 14 can enter the dispenser. The lower arm 41B is then in position under the diaphragm next to the topmost one and thus provides firm support for the topmost diaphragm as the stethoscope head is pushed into the dispenser.

A further device for firmly supporting the topmost diaphragm is shown in FIGS. 12A through 12D. FIGS. 12A and 12C are views in vertical section of the top part of a dispenser with several diaphragms in place. FIGS. 12B and 12D are top plan views of the top of the dispenser with no diaphragms in place. This device consists essentially of two opposed plates 52 and 52A which, when activated, support the topmost diaphragm and when at rest are retracted so as not to engage a diaphragm. FIGS. 12A and 12B show the rest position and FIGS. 12C and 12D the activated position. Plates 52 and 52A are connected to knobs 50 and 50A which are spring-loaded by springs 51 and 51A to keep the device in its rest position unless the knobs are manually pressed inward. As shown, the shape of the each plate is approximately lunate, being defined by two radii of the circular cylindrical dispenser and two arcs between the radii.

The embodiment shown in FIG. 13A employs a helical screw, such as is commonly used in lipstick holders, instead of a pushing spring 23. The left part, shown in section, represents a portion of the dispenser with diaphragms in place. The right part, in front elevation, shows only a portion of bottom 35 and outer shell 31. In this embodiment, the dispenser consists of three separate parts, which are shown in isometric drawing in FIGS. 13B–13D. The outer shell is a circular cylinder 31 which is open at both ends and has inside a helical grooves 32 which leads from near the bottom of the shell to near the top, suitably in two turns. The diaphragms are supported on an inner support plate 33 which has two knob-like projections 34, spaced 180 degrees apart, which ride in groove 32. The main body of the dispenser consists of bottom 35 and of a thin cylindrical wall 36 which is integral with the bottom and is located just inside shell 31, spaced away from shell 31 sufficiently to permit shell 31 to rotate around wall 36. Wall 36 has a vertical slit which lies in the plane of the drawing and is slightly wider than projection 34 of the inner support plate. As outer shell 31 and bottom 35 are twisted with respect to each other, the inner support plate 33, which carries the diaphragms, can be made to ride up or down with respect to the body of the dispenser. It can thus be brought to the position where the topmost diaphragm is even with the top of the outer shell and inner wall. In other modifications of this basic system, not shown, a ratchet device may be provided so that after each partial turn, sufficient to move a fresh diaphragm to the top, downward movement is prevented by a positive stop. After the dispenser has been emptied, the ratchet is returned to its original neutral position for insertion of a new cartridge or set of diaphragms.

In another mode of the invention, the stethoscope head and diaphragm do not employ the ring-and-groove system described above, but utilize instead a releasable contact adhesive. For purposes of this description, a releasable contact adhesive is a material which, when applied to one of the diaphragm surface or the stethoscope surface, will permit the diaphragm and stethoscope head, upon contact, to adhere firmly to each other, but will permit the diaphragm to be readily pulled off for disposal. Such adhesives are commercially available materials.

The adhesive is most suitably applied to the face of the diaphragm which contacts the stethoscope head, in an annular area which corresponds to the solid portion of the planar surface of the stethoscope head or diaphragm retaining ring. This system may also be combined with the use of magnetism to enhance adhesion. Magnetic or magnetizable material may be incorporated into the adhesive, or emplaced in the portion of each diaphragm which corresponds to the part that contacts the stethoscope head.

The diaphragms stored in the dispenser will have to be separated by sheets of paper which do not adhere to the adhesive. When a diaphragm is to be replaced, the old diaphragm is pulled off by means of the tab or projecting portion, the separating paper is removed from the top of the dispenser and the stethoscope head is inserted and then removed with the new diaphragm adhering by means of the adhesive. In an embodiment which facilitates removal of the paper, the papers, as well as the diaphragms, have tabs which project through slits in the wall of the dispenser. The paper then is easily removed by means of the tabs.

This invention can also solve another problem associated with the medical use of stethoscopes. Stethoscope heads are often relatively cold and cause discomfort to the patient being examined. The diaphragm dispenser of this invention may be modified to allow the diaphragm to be heated to a temperature comfortable to the touch. This can be accomplished, for example, by providing heating elements in the dispenser wall without touching the diaphragms,—or in the bottom, if the walls are of heat-conducting material—and placing a battery for operating the heating elements in the dispenser bottom.

Many other modifications may be made within the scope of the invention, as claimed in the attached claims.

I claim as my invention:
1. In combination,
   a. a stethoscope having a head which has a flat outer annular plane surface, said surface having a circular groove;
   b. a rigid flat diaphragm adapted to fit over said annular plane surface, said diaphragm having on one surface a projection adapted to fit into said circular groove;
   wherein said head and diaphragm are constructed to be held in firm but readily releasable contact and
   wherein said diaphragm projects in whole or in part beyond said annular plane surface; and
   c. a dispensing container adapted to hold a plurality of said diaphragms arranged in a column, said container having an open end adapted to admit the head of said stethoscope to be pressed against the diaphragm nearest said open end and to be withdrawn with said nearest diaphragm firmly attached to said head and means to support said column of diaphragms against the pressure of said head.
2. A combination according to claim 1 wherein the outer surface of said head is on a retaining ring.
3. In combination,
   a. a stethoscope having a head which has a flat outer annular plane surface;
   b. a rigid flat diaphragm adapted to fit over said annular plane surface, said diaphragm having on one surface an annular area of releasable contact adhesive corresponding at least in part to said annular plane surface;
   wherein said head and diaphragm are constructed to be held in firm but readily releasable contact and
   wherein said diaphragm projects in whole or in part beyond said annular plane surface; and
   c. a dispensing container adapted to hold a plurality of said diaphragms arranged in a column, said container having an open end adapted to admit the head of said stethoscope to be pressed against the diaphragm nearest said open end and to be withdrawn with said nearest diaphragm firmly attached to said head and means to support said column of diaphragms against the pressure of said head.
4. A combination according to claim 3 wherein the outer surface of said head is on a retaining ring.
5. In combination,
   a. a stethoscope having a head adapted for quick firm attachment and quick release of a suitably equipped diaphragm; and
   b. a dispensing container adapted to hold a plurality of said diaphragms arranged in a column, said container having an open end adapted to admit the head of said stethoscope to be pressed against the diaphragm nearest said open end and to be withdrawn with said nearest diaphragm firmly attached to said head.
6. A combination accordng to claim 5 wherein said stethoscope has a head which has flat outer annular plane surface, said surface having a circular groove adapted to engage a rigid flat diaphragm adapted to fit over said annular surface and project in whole or in part beyond said surface and having, on a surface facing the stethoscope when in place in said container, a projection adapted to fit into said circular groove, said head and diaphragms being constructed to be held, when engaged, in firm but readily releasabable contact.
7. A combination according to claim 6 wherein said stethoscope head contains magnetic or magnetizable material positioned to attract corresponding magnetizable or magnetic material in the projection on a dia- phragm which contains, correspondingly, magnetizable or magnetic material.

8. A combination according to claim 6 wherein the outer surface of said head is on a retaining ring.

9. A combination according to claim 5 wherein said stethoscope has a head which has a flat outer annular plane surface adapted to engage a rigid flat diaphragm adapted to fit over said annular plane surface and project in whole or in part beyond said surface and having, on the surface facing the stethoscope when in place in said container, an annular area of releasable contact adhesive corresponding at least in part to said annular plane surface.

10. A combination according to claim 9 wherein said stethoscope head contains magnetic or magnetizable material positioned to attract corresponding magnetizable or magnetic material in a diaphragm which contains, correspondingly, magnetizable or magnetic material.

11. A combination according to claim 9 wherein the outer surface of said head is on a retaining ring.

12. A container for dispensing stethoscope diaphragms comprising
   a. a cylindrical body adapted to hold a plurality of said diaphragms as a column, said cylindrical body having an open end adapted to admit a stethoscope head,
   b. spring means adapted to urge said column of diaphragms toward said open end, and
   c. displaceable diaphragm holding means at said open end;
said holding means adapted to hold said column of diaphragms in place and to be displaced sufficiently to admit the head of a stethoscope.

13. A container according to claim 12 comprising means for heating the diaphragms contained therein to a temperature comfortable to the touch.

14. In combination,
   a. a stethoscope having a head which has a flat outer annular plane surface, said surface having a circular groove; and
   b. a rigid flat diaphragm adapted to fit over said annular plane surface, said diaphragm having on one surface a projection adapted to fit into said circular groove;
wherein said head and diaphragm are adapted to be held in firm but readily releasable contact; and wherein:
   i. said stethoscope head contains magnetic or magnetizable material positioned to attract corresponding magnetizable or magnetic material in the projection on said diaphragm;
   ii. said projection contains such corresponding magnetizable or magnetic material; and
   iii. said diaphragm, when in contact with said annular plane surface, projects in whole or in part beyond the plane surface;
whereby said diaphragm can be quickly and tightly attached to said stethoscope held by being pressed against said head and quickly and easily removed by a pull exerted on a portion of the diaphragm which projects beyond said annular plane surface.

15. A combination according to claim 14 wherein said magnetic or magnetizable material in the stethoscope head is located near said circular groove.

16. A combination according to claim 14 wherein the outer surface of said head is on a retaining ring.

17. In combination,
   a. a stethoscope having a head which has a flat outer annular plane surface; and
   b. a rigid flat diaphragm adapted to fit over said annular plane surface;
wherein said head and diaphragm are adapted to be held in firm but readily releasable contact; and wherein:
   i. said diaphragm has on one surface an annular area of releasable contact adhesive corresponding at least in part to said annular plane surface;
   ii. said stethoscope head contains magnetic or magnetizable material;
   iii. said diaphragm contains, correspondingly, magnetizable or magnetic material;
   iv. said diaphragm, when in contact with said annular plane surface, projects in whole or in part beyond the plane surface; and
   v. said firm contact is the result of a combination of adhesion and magnetic attraction;
whereby said diaphragm can be quickly and tightly attached to said stethoscope head by being pressed aganst said head and quickly and easily removed by a pull exerted on a portion of the diaphragm which projects beyond said annular plane surface.

18. A combination according to claim 17 wherein the outer surface of said head is on a retaining ring.

* * * * *